United States Patent

Ochsner et al.

[11] 4,006,109
[45] Feb. 1, 1977

[54] TRIMETHYL NONENE ALCOHOLS AND PERFUME COMPOSITIONS

[75] Inventors: Paul Albert Ochsner, Geneva; Karl-Fred De Polo, Onex, both of Switzerland

[73] Assignee: Givaudan Corporation, Clifton, N.J.

[22] Filed: Mar. 10, 1975

[21] Appl. No.: 556,991

[30] Foreign Application Priority Data

Mar. 15, 1974 Switzerland .................. 3628/74

[52] U.S. Cl. .................... 252/522; 260/632 R
[51] Int. Cl.[2] ............................ C11B 9/00
[58] Field of Search ............ 252/522; 260/632 R

[56] References Cited

UNITED STATES PATENTS

| | | | |
|---|---|---|---|
| 3,394,169 | 7/1968 | Davis | 260/632 R |
| 3,674,846 | 7/1972 | Brendel | 260/632 R |
| 3,859,366 | 1/1975 | Schleppnik | 260/632 R |

FOREIGN PATENTS OR APPLICATIONS

| | | | |
|---|---|---|---|
| 1,802,121 | 6/1969 | Germany | 252/522 |
| 2,146,158 | 4/1972 | Germany | 252/522 |

OTHER PUBLICATIONS

Chem. Ab. 78, 110458y, 1973.
Chem. Ab. 72, 121721f, 1970.
Houben—Weyl, Method of Organic Chemistry, George Thieme Verlag—Stuttgart, Germany 4, Bd V1R, 1972, p. 60, p. 62, p. 70.

*Primary Examiner*—Veronica O'Keefe
*Attorney, Agent, or Firm*—Thomas Cifelli, Jr.

[57] ABSTRACT

Novel odorants of the formula:

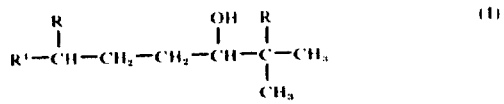

where one of the R's is a hydrogen atom and the other is a methyl group and R' is either the 1- or 2- isobutenyl group.

Their use in odorant compositions, method or preparing such alcohols and compositions and novel intermediates for I are also disclosed.

5 Claims, No Drawings

TRIMETHYL NONENE ALCOHOLS AND PERFUME COMPOSITIONS

FIELD OF THE INVENTION

This invention relates to novel alcohols and odorant compositions containing them.

SUMMARY OF THE INVENTION

The novel alcohols provided by the present invention have the formula I given above.

The novel alcohols are made by treating a diol of the formula:

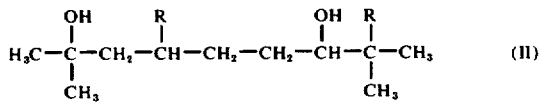

wherein R has the significance given earlier, with a dehydrating agent.

DESCRIPTION OF THE PREFERRED EMBODIMENTS

As aforesaid, the novel alcohols provided by the present invention have the following general formula

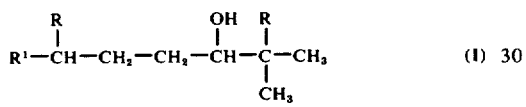

wherein one of the R symbols represents a hydrogen atom and the other represents the methyl group and the symbol $R^1$ represents the 1- or 2-isobutenyl group.

It will be appreciated that formula I hereinbefore embraces alcohols of the following formulae:

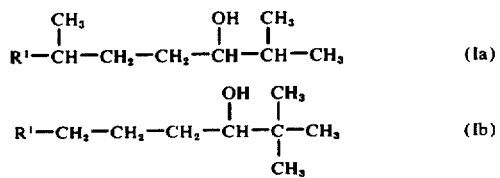

wherein $R^1$ has the significance given earlier.

By formula Ia and Ib there are accordingly included the alcohols 2,6,8-trimethyl-7(or 8)-nonen-3-ol or 2,2,8-trimethyl-7(or 8)-nonen-3-ol as well as the corresponding isomeric mixtures.

According to the process provided by the present invention, the alcohols of formula I hereinbefore are manufactured by treating a diol of the general formula

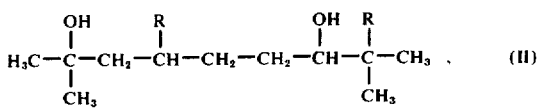

wherein R has the significance given earlier, with a dehydrating agent.

The partial dehydration of a diol of formula II can be carried out according to known methods. The dehydration yields a mixture of isomeric compounds which are differentiated by the position of the double bond introduced ($R^1$ = 1-isobutenyl or 2-isobutenyl). Separation of the isomeric mixture into the individual components is possible (e.g. for the mixture Ia by distillation such as by means of a spinning-band column) but is usually not necessary.

Suitable dehydrating agents are, for example, acidic salts (e.g. potassium bisulphate) with which yields up to 90% of theory can be obtained. However, there can also be used other catalysts which are known to be useful for the dehydration of tertiary alcohols such as iodine, phosphoric acid, boric acid, oxalic acid, toluenesulphonic acid and the like.

The dehydrating agent can generally be used without a solvent. When potassium bisulphate is used as the dehydrating agent, the diol of formula II is expediently warmed (e.g. under reduced pressure such as under a water-jet vacuum) to a temperature of ca 120°–145° C, the alcohol of formula I and the water formed during the dehydration distilling off. There can, however, also be added an organic solvent such as carbon tetrachloride, benzene, toluene or the like, the water formed during the dehydration being distilled off azeotropically with such solvent.

The alcohol of formula I can be isolated from the reaction mixture; for example, by distillation.

The diol starting materials of formula II can be prepared according to the following formula scheme in which R has the significance given earlier:

Formula Scheme

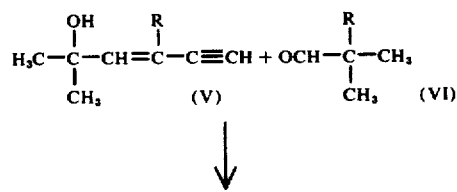

-continued

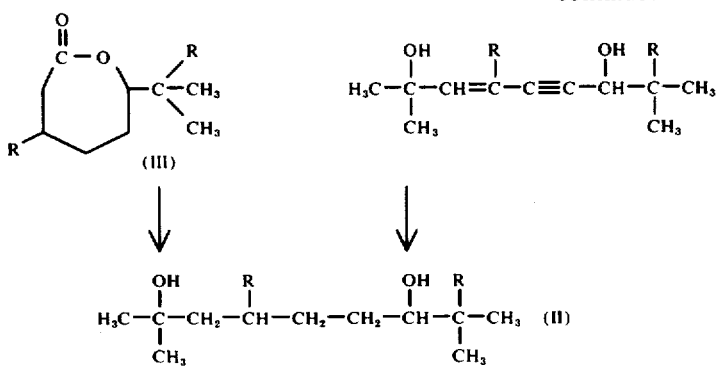

By treatment of a Σ-lactone of a substituted 6-hydroxycaprylic acid of formula III with a methylmagnesium halide under the conditions of a Grignard reaction, a diol of formula II is obtained directly.

On the other hand, a Grignard reagent produced from an unsaturated alcohol of formula V and ethylmagnesium bromide can be condensed with an aldehyde of formula VI to give an unsaturated diol of formula IV. Catalytic hydrogenation of an unsaturated diol of formula IV yields a diol of formula II.

The alcohols of formulae Ia and Ib hereinbefore or the isomeric mixtures obtained during thier manufacture ($R^2 = $ 1-isobutenyl and 2-isobutenyl) possess particular odorant properties. The mixture Ia provides a green, flowery, fruity, leathery, slightly menthol-like odour which is reminiscent of ivy. The odour of the isomeric mixture Ib is fruity, flowery, fresh and lavender-like. It is reminiscent of the odour of a blossoming lavender field. Because of their interesting olefactory properties, the two isomeric mixtures can be used as odorants; for example, in perfumery for the manufacture of odorant compositions such as perfumes or for the perfuming of products of all types such as, for example, soaps, washing agents, solid and liquid detergents, aerosols or other cosmetic products such as ointments, face milks, make-up, lipsticks, bath salts, bath oils and the like.

Having regard to its very natural note of ivy leaves and its leather note, the isomeric mixture Ia is especially suitable for modifying the odour of known compositions; for example, those of the chypre and fougere type. The addition of the alcohols of formula Ia to such compositions imparts a natural and fresh note thereto. Similar effects are produced by the addition of the alcohols of formula Ib.

The concentration of a mixture of formula I can vary within wide limits depending on the intended use. For example, the concentration can vary from between about 1 wt. % in the case of detergents and about 15 wt. % in the case of alcoholic solutions. In perfume bases of concentrates, the concentrations can, of course, also be higher.

The following Examples illustrate the manner in which the alcohols provided by this invention can be manufactured:

EXAMPLE 1

30 g of potassium bisulphate are added to a Claisen flask which is provided with a thermometer, condenser and dropping funnel. The flask is heated to 110°–120° C in an oil bath evacuated to a pressure of 12 mm Hg and there are then added dropwise 160 g of 2,4,8-trimethyl-nona-2,7-diol. A mixture of water and 2,6,8-trimethyl-7(and 8)-nonen-3-ol distills off between 60° C and 112° C. The water is separated and the distillate taken up in ether, washed with sodium bicarbonate and then with water until a neutral reaction is obtained. The crude product is distilled, 100 g (69%) of a mixture of 2,6,8-trimethyl-7(and 8)-nonen-3-ol being obtained. Boiling point = 93°–94°C/5 mm Hg; $n_D^{20} = 1.4525$; $d_4^{20} = 0.8468$. IR spectrum: R,R'C=CH$_2$: 3063 cm$^{-1}$ ($\nu$CH); 1645 cm$^{-1}$ ($\nu$C=C), 885 cm$^{-1}$ ($\delta$CH), R,R'C = CHR": 1670 cm$^{-1}$ ($\nu$C=C); 840 cm$^{-1}$ ($\delta$CH), secondary alcohol: 3350 cm$^{-1}$ (strong, wide).

By distillation on a spinning-band column (Nester-Faust), there are obtained the individual isomers having the following data:

1. 2,6,8-Trimethyl-7-nonen-3ol: Boiling point 69°–70° C/1 mm Hg; $n_D^{20} = 1.4530$; IR spectrum: triple-substituted double bond: 840 cm$^{-1}$ ($\delta$CH), secondary alcohol: 3360 cm$^{-1}$ (strong, wide; polymer associations). Odour: green towards ivy, towards roses, towards amysalicylate.

2. 2,6,8-Trimethyl-8-nonen-3-ol: Boiling point 70°–71° C/1 mm Hg; $n_D^{20} = 1.4520$; IR spectrum: characteristic bands for R,R!C=CH$_2$: 3070 cm$^{-1}$ ($\nu$CH), 1650 cm$^{-1}$ ($\nu$C=C), 890 cm$^{-1}$ ($\delta$CH); secondary alcohol 3370 cm$^{-1}$, Odour: as 1), but more flowery, heavier, more tenacious, stronger.

The 2,4,8-trimethyl-nona-2,7-diol used as the starting material can be prepared as follows:

A. In a 5-liter round-bottomed flask provided with a thermometer, stirrer, condenser and dropping funnel, methylmagnesium iodide is prepared from 63.2 g (2.6 gram-atom) of magnesium and 340 g (2.4 mol) of methyl iodide in 1.5 liters of dry ether. There are then added 170 g of the Σ-lactone of 6-hydroxy-3,7-dimethylcaprylic acid in 300 ml of dry toluene. After the addition, the mixture is held for 2 hours at reflux temperature and then cooled in an ice-bath. The magnesium complex formed is decomposed by the addition of a solution of 200 g of ammonium chloride in 2 liters of water. The organic phase is separated and the aqueous layer extracted four times with 300 ml of ether each time. The combined organic phases are washed with 5% tartaric acid, water and an 8% aqueous sodium bicarbonate solution and then washed neutral with water. The solvents are evaporated and the crude product distilled. There are thus obtained 162 g (80%) of 2,4,8-trimethyl-nona-2,7diol of boiling point 75°–77° C/0.01 mm Hg; $n_D^{20} = 1.4598$.

B. Ethylmagnesium bromide is prepared from 24.3 g (1 gram-atom) of magnesium and 114.5 g (1.05 mol) of ethyl bromide in 500 ml of dry ether.

There are then added 150 ml of dry benzene and subsequently, while stirring and at a temperature between 30° C and 40° C, a solution of 55.9 g (0.45 mol) of 2,4-dimethyl-hex-3-en-5-yn-2-ol in 100 ml of dry benzene. After the addition, the mixture is held for 3 hours at 50° C and then cooled to 10° C. There is then added, within 1 hour at a temperature between 10° C and 20° C, a solution of 31.3 g (0.435 mol) of isobutyraldehyde in 100 ml of benzene. The mixture is left to stand for 12 hours at room temperature and then added with stirring to a solution of 40 g of ammonium chloride in 200 ml of ice-water. In order to facilitate separation of the phases, 53 ml of glacial acetic acid are added. The organic phase is separated and the aqueous layer extracted twice with ether. The combined extracts are washed neutral with a saturated sodium bicarbonate solution and a saturated sodium chloride solution and, after the addition of a small amount of hydroquinone, dried over sodium sulphate. After evaporation of the solvent (<40° C), there are obtained 92.3 g of crude 2,4,8-trimethyl-non-3-en-5-yne-2,7-diol which are immediately hydrogenated as follows: To a 1 liter magnetically stirred autoclave having built-in cooling spirals, there are added 92.3 g of crude 2,4,8-trimethyl-non-3-en-5-yne-2,7-diol, 5 g of Raney nickel, 0.5 g of Raney nickel, 0.5 g of anhydrous sodium carbonate and 125 ml of absolute methanol. The mixture is first hydrogenated while cooling with water at a pressure of ca 8 atmospheres. After the initial strongly exothermic reaction has ended, the mixture is hydrogenated up to complete saturation at 30 atmospheres of hydrogen and 80° C. After cooling, the catalyst is filtered off from the mixture, the alcohol removed on a rotary evaporator and the residue distilled over a small amount of sodium carbonate. There are thus obtained 70.6 g (74%) of 2,4,8-trimethyl-nona-2,7-diol of boiling point 130°–133° C/5 mm Hg; $n_D^{20} = 1.4600$.

EXAMPLE 2

According to the procedure described in Example 1, from 155.6 g. of 2,8,8-trimethyl-nona-2,7-diol and 15 g of potassium bisulphate there are obtained, at 120°–150° C/13 mm Hg, 112.3 g (79.4%) of 2,2,8-trimethyl-7(and 8)-nonen-3-ol. Boiling point = 101°–102° C/12 mm Hg; $n_D^{20} = 1.4520$; $d_4^{20} = 0.8532$. IR spectrum: (alcohol function): 3395 cm$^{-1}$; R,R'C=CH$_2$: 3070 cm$^{-1}$ ($\nu$CH), 1650 cm$^{-1}$ ($\nu$C=C), 890cm$^{-1}$ ($\delta$CH); R,R'C=CHR'': 1670 cm$^{-1}$ ($\nu$C=C; very weak), 840 cm$^{-1}$ ($\delta$CH).

The 2,8,8-trimethyl-nona-2,7-diol used as the starting material is prepared from 170.2 g of the Σ-lactone of 6-hydroxy-7,7-dimethylcaprylic acid and methylmagnesium iodide according to the procedure described in Example 1, the decomposition of the magnesium complex being carried out using 150 ml of acetic acid. Yield: 155.6 g (77%); boiling point 130° C/5 mm Hg; melting point 63°–64° C; $n_D^{20} = 1.4508$.

The 6-hydroxy-7,7-dimethylcaprylic acid Σ-lactone can be obtained as follows:

To a 3-liter round-bottomed flask provided with a stirrer, thermometer, condenser and dropping funnel, there are added 353 g (2.3 mol) of 2-tert. butyl-cylochexanone, 14 g of anhydrous sodium acetate and 1.17 liters of methylene chloride. 370 g of ca. 40% peracetic acid are added at room temperature while cooling. The mixture is held first at room temperature for 20 hours with stirring and then for a further 48 hours under reflux temperature. After cooling, the mixture is poured on to ice, the layers are separated and the organic layer washed with an iron sulphate solution and then with water until a neutral reaction is obtained. The solvent is distilled off and the crude lactone distilled, there being obtained 274 g (70.3%) of the Σ-lactone of 6-hydroxy-7,7-dimethylcaprylic acid of boiling point 134° C/12 mm Hg; melting point 54°–58° C.

The following Example illustrates typical odorant compositions containing the alcohols provided by this invention:

EXAMPLE A

A. Compositions containing a mixture of 2,6,8-trimethyl-7(and 8)-nonen-3-ol.

| 1. Fougère composition | Parts by weight |
|---|---|
| 2,6,8-Trimethyl-7(and 8)-nonen-3-ol | 100 |
| Coumarin | 10 |
| Patchouli oil | 20 |
| Eugenol | 20 |
| Sage clary oil (Sauge Sclarée) | 20 |
| Heliotropin | 20 |
| Isoraldein 70 (mixture of n- and iso-methyl-α- and β-ionone) | 30 |
| Geraniol | 30 |
| Sandalwood oil | 40 |
| Vetiver oil | 40 |
| Lemon oil | 40 |
| Citronellol | 40 |
| Linalyl acetate | 50 |
| Musk ambrette | 50 |
| Petitgrain oil Paraguay | 50 |
| Geranium oil Bourbon | 60 |
| Oak-moss abs. Yugoslavian | 80 |
| Lavender oil (French) | 150 |
| Amyl salicylate | 150 |
| | 1000 |

| 2. Cologne composition | Parts by weight |
|---|---|
| 2,6,8-Trimethyl-7(and 8)-nonen-3-oil | 100 |
| Citral B 100LG (citral containing 5% citronellal) | 10 |
| Clove | 10 |
| Cananga oil | 10 |
| Mandarin oil | 20 |
| Neroli Bigarade | 20 |
| Methylanthranilate 10% in Carbitol (diethyleneglycol monoethyl ether) | 20 |
| Rosemary oil | 30 |
| Musk ketone | 30 |
| Lavender oil (French) | 50 |
| Petitgrain oil | 50 |
| Linalyl acetate | 100 |
| Bergamot oil | 150 |
| Lemon oil | 400 |
| | 1000 |

The hesperidin note of the foregoing composition is modified in an extremely pleasant manner by the ivy-leaf note of 2,6,8-trimethyl-7(and 8)-nonen-3-ol.

| 3. Gardenia composition | Parts by weight |
|---|---|
| 2,6,8-Trimethyl-7(and 8)-nonen-3-ol | 150 |
| Peche 10% in Carbitol | 10 |
| Indol 10% in Carbitol | 10 |
| Heliotropin | 10 |
| Styrax oil | 10 |
| Benzyl acetate | 20 |
| Hydroxycitronellal | 20 |
| Methyl benzoate | 30 |
| Linalyl acetate | 30 |
| Prunolide 10% in Carbitol | 30 |

| 3. Gardenia composition | Parts by weight |
| --- | --- |
| Dimethylbenzyl-carbinyl-acetate | 50 |
| Ylang Ylang Extra | 50 |
| Phenylethyl alcohol | 80 |
| α-Irisone | 100 |
| α-Hexyl-cinnamaldehyde | 100 |
|  | 700 |

The green note of this composition, which is normally produced by adding gardenol (methyl-phenylcarbinyl acetate), is effected here by means of 2,6,8-trimethyl-7(and 8)-nonen-3-ol. By this means, the bouquet of the composition becomes more rounded-off.

B. Compositions containing a mixture of 2,2,8-trimethyl-7(and 8)-nonen-3-ol.

| 1. Fougère composition | Parts by weight |
| --- | --- |
| 2,2,8-Trimethyl-7(and 8)-nonen-3-ol | 220 |
| Patchouli oil | 20 |
| Eugenol | 20 |
| Sauge Sclarée | 20 |
| Heliotropin | 20 |
| Coumarin | 20 |
| Geraniol | 30 |
| Sandalwood oil | 40 |
| Isoraldein (α-iso-methyl-ionone) | 40 |
| Citronellol | 40 |
| Linalool | 40 |
| Linalyl acetate | 50 |
| Musk ambrette | 50 |
| Bergamot oil | 50 |
| Lavender oil (French) | 50 |
| Geranium oil | 60 |
| Oak-moss abs. (Yugoslavian) | 80 |
| Amyl salicylate | 150 |
|  | 1000 |

In the foregoing composition, the spicy lavender note is produced exclusively by the addition of 2,2,8-trimethyl-7(and 8)-nonen-3-ol. Hitherto, in order to produce this lavender note, there have been required a number of components such as lavender oil, lavandin oil, lavender and lavandin concret, methylamylketone linalyl acetate, linalool and the like.

| 2. Cologne composition | Parts by weight |
| --- | --- |
| 2,2,8-Trimethyl-7(and 8)-nonen-3-ol | 50 |
| Citral base (ca 1/3 neral and 2/3 geranial) | 5 |
| Eugenol | 5 |
| Estragole | 5 |
| Thyme oil | 10 |
| Rosemary oil | 10 |
| Indol (10% Carbitol) | 15 |
| Isoraldein (α-iso-methyl-ionone) | 20 |
| Hydroxycitronellal | 30 |
| Patchouli oil | 30 |
| Petitgrain oil (French) | 30 |
| Bergamot oil | 50 |
| Benzyl acetate | 50 |
| Vetiver acetate | 50 |
| Orange oil (Guinea) | 50 |
| Linalool | 60 |
| Lavandin | 70 |
| Lemon oil | 80 |
| α-Hexyl-cinnamaldehyde | 80 |
| Linalyl acetate | 100 |
|  | 800 |

The presence of 2,2,8-trimethyl-7(and 8)-nonen-3-ol makes an extraordinary contribution to the fresh and natural notes of this composition.

The crude 2,4,8-trimethyl-non-3-en-5-yne-2,7-diol made in accordance with Example 1 may be purified by bulb tube destillation. The boiling point of the pure compound is 105° C/0,02 mmHg; $n_D^{20} = 1,4940$.

The aforesaid Σ-lactone of 6-hydroxy-3,7-dimethyl capyrilic acid (Example 1A) is a known compound. See, e.g., Chem. Ber. 32, 3619(1899), 3625(1899).

The aforesaid 2,4-dimethyl-hex-3-en-5-yn-2-ol (Example 1B) is a known compound. See, e.g., J. Chem. Soc. 90, (1945).

What is claimed is:

1. An odorant composition which comprises an olfactorily-effective amount of an alcohol of formula I given in claim 1 and at least one other olfactory agent.

2. An odorant composition according to claim 1, wherein said alcohol is 2,6,8-trimethyl-7(and 8)-nonen-3-ol.

3. An odorant composition according to claim 1, wherein said alcohol is 2,2,8-trimethyl-7(and 8)-nonen-3ol.

4. An odorant composition according to claim 1, wherein said alcohol is 2,6,8-trimethyl-7-nonen-3-ol.

5. An odorant composition according to claim 1, wherein said alcohol is 2,6,8-trimethyl-8-nonen-3-ol.

* * * * *